(12) United States Patent
ColDepietro et al.

(10) Patent No.: US 6,273,260 B1
(45) Date of Patent: Aug. 14, 2001

(54) PHARMACEUTICAL PACKAGING SYSTEM

(75) Inventors: Ralph ColDepietro, West Chester, PA (US); Daniel F. Lynch, Mooresville, IN (US)

(73) Assignee: Eli Lilly and Company, Indianapolis, IN (US)

( * ) Notice: Subject to any disclaimer, the term of this patent is extended or adjusted under 35 U.S.C. 154(b) by 0 days.

(21) Appl. No.: 09/520,946

(22) Filed: Mar. 8, 2000

(51) Int. Cl.[7] .................................................. B65D 83/04
(52) U.S. Cl. ......................... 206/532; 206/534; 206/459.5
(58) Field of Search ................................... 206/528, 530, 206/531, 532, 534, 538, 539, 459.1, 459.5; 40/360, 638; 53/467, 473, 475

(56) References Cited

U.S. PATENT DOCUMENTS

| | | | |
|---|---|---|---|
| 3,324,995 | * 6/1967 | Sharp, Jr. | 206/534 |
| 4,314,081 | 2/1982 | Molloy et al. . | |
| 4,626,549 | 12/1986 | Molloy et al. . | |
| 4,883,180 | * 11/1989 | Humphrey et al. | 206/534 |
| 4,913,083 | * 4/1990 | Valvo et al. | 206/534 |
| 4,955,481 | * 9/1990 | Novinski et al. | 206/534 |
| 4,974,729 | * 12/1990 | Steinnagel | 206/534 |
| 5,019,302 | 5/1991 | Sparks et al. . | |
| 5,100,592 | 3/1992 | Sparks et al. . | |
| 5,242,055 | * 9/1993 | Pora | 206/532 |
| 5,833,072 | * 11/1998 | Lambelet, Jr. | 206/534 |
| 5,910,319 | 6/1999 | Anderson et al. . | |
| 6,024,222 | * 2/2000 | Friberg et al. | 206/531 |

* cited by examiner

Primary Examiner—Luan K. Bui
(74) Attorney, Agent, or Firm—Michael T. Rates; Robert D. Titus

(57) ABSTRACT

A packaging system for storing and dispensing individual doses of medication on prescribed days, the packaging system comprising a series of sheets adapted to fold over each other with doses of medication removably held thereon. A plurality of labels are held on at least one of the sheets, each label corresponding to one dose of medication, each of the labels being adapted to be removed from one of the sheets and applied to a calendar to thereby serve as a reminder of the day on which the corresponding individual dose of medication is to be taken. The packaging system may further comprise a sleeve with one open end, the open end and the sleeve engaging the sheets when in a folded state.

35 Claims, 6 Drawing Sheets

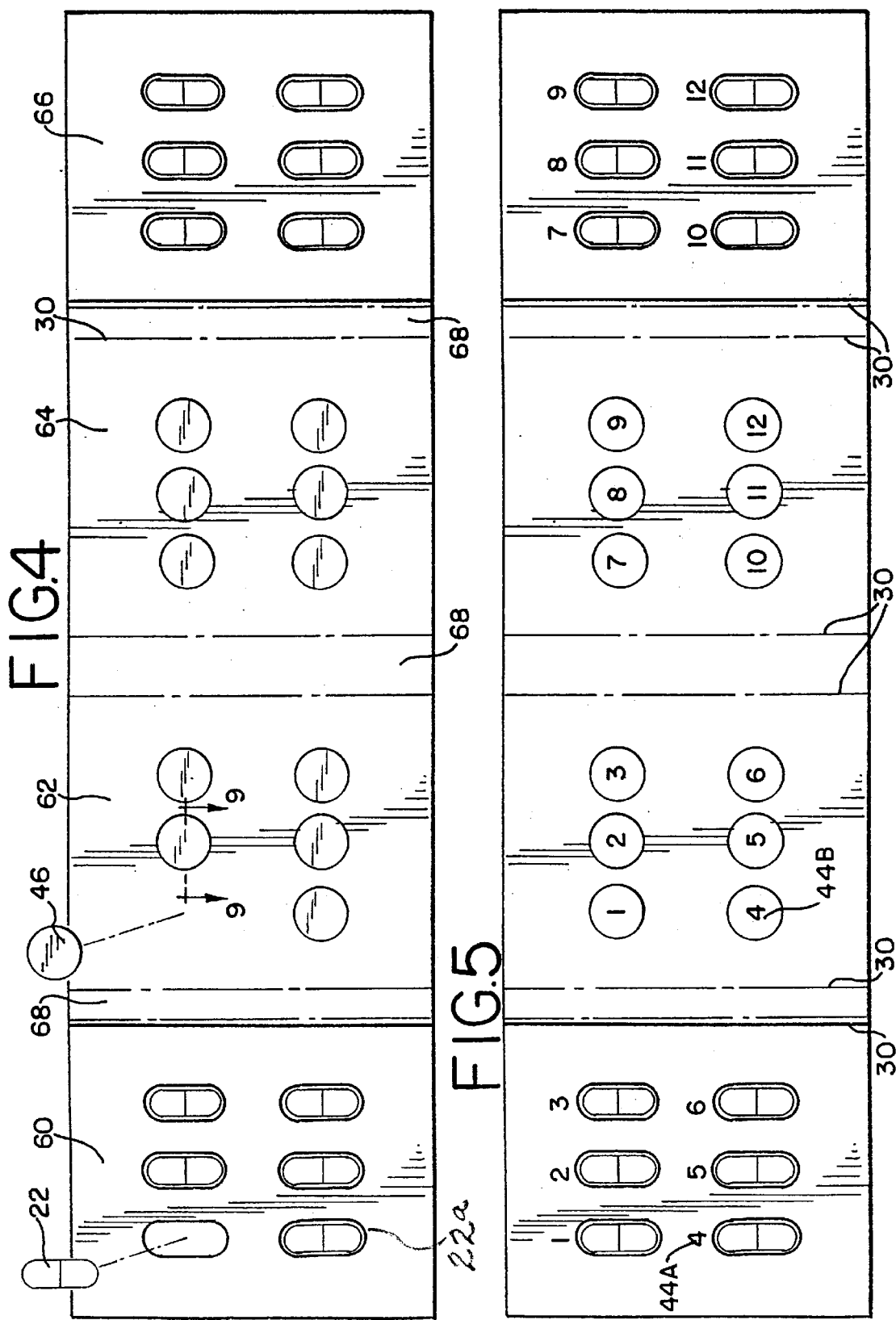

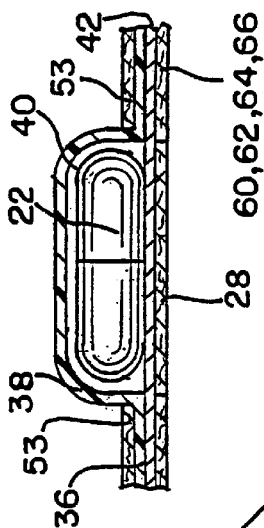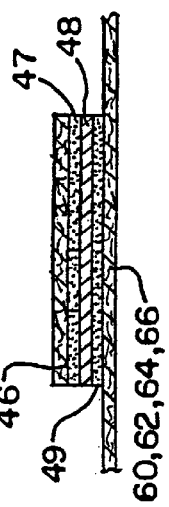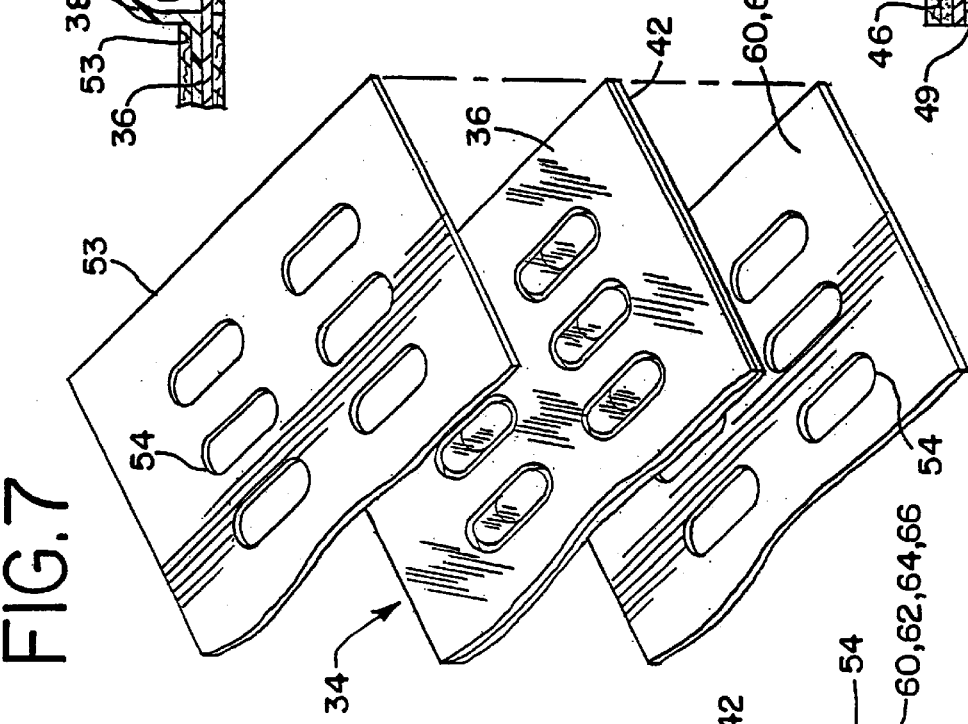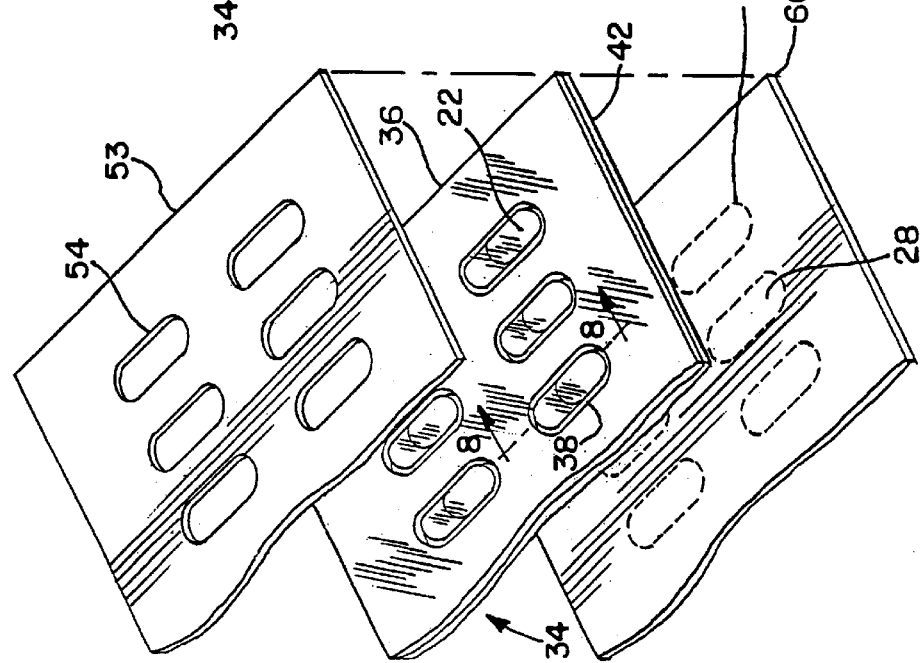

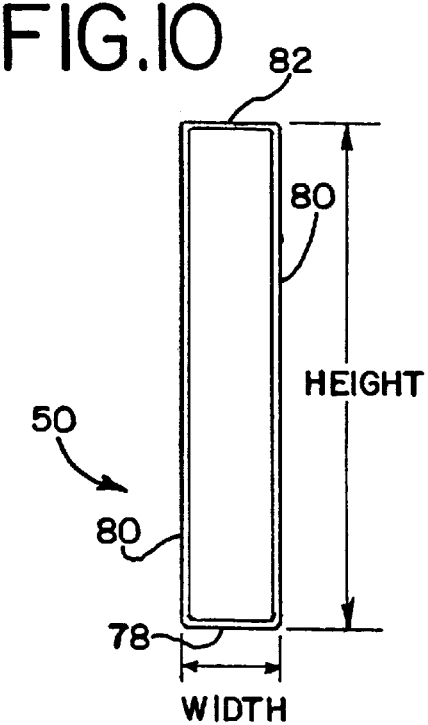
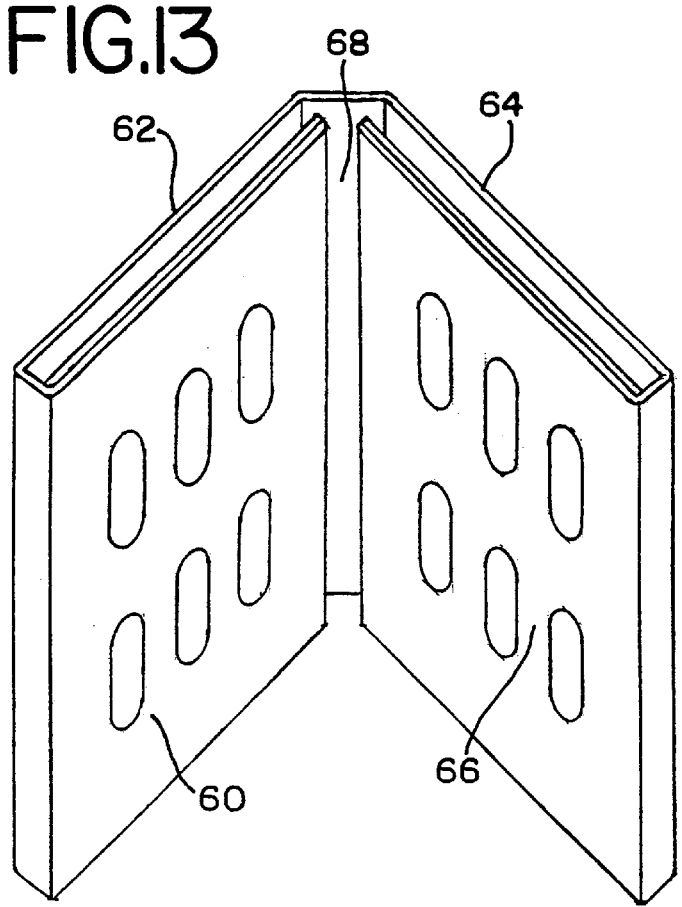

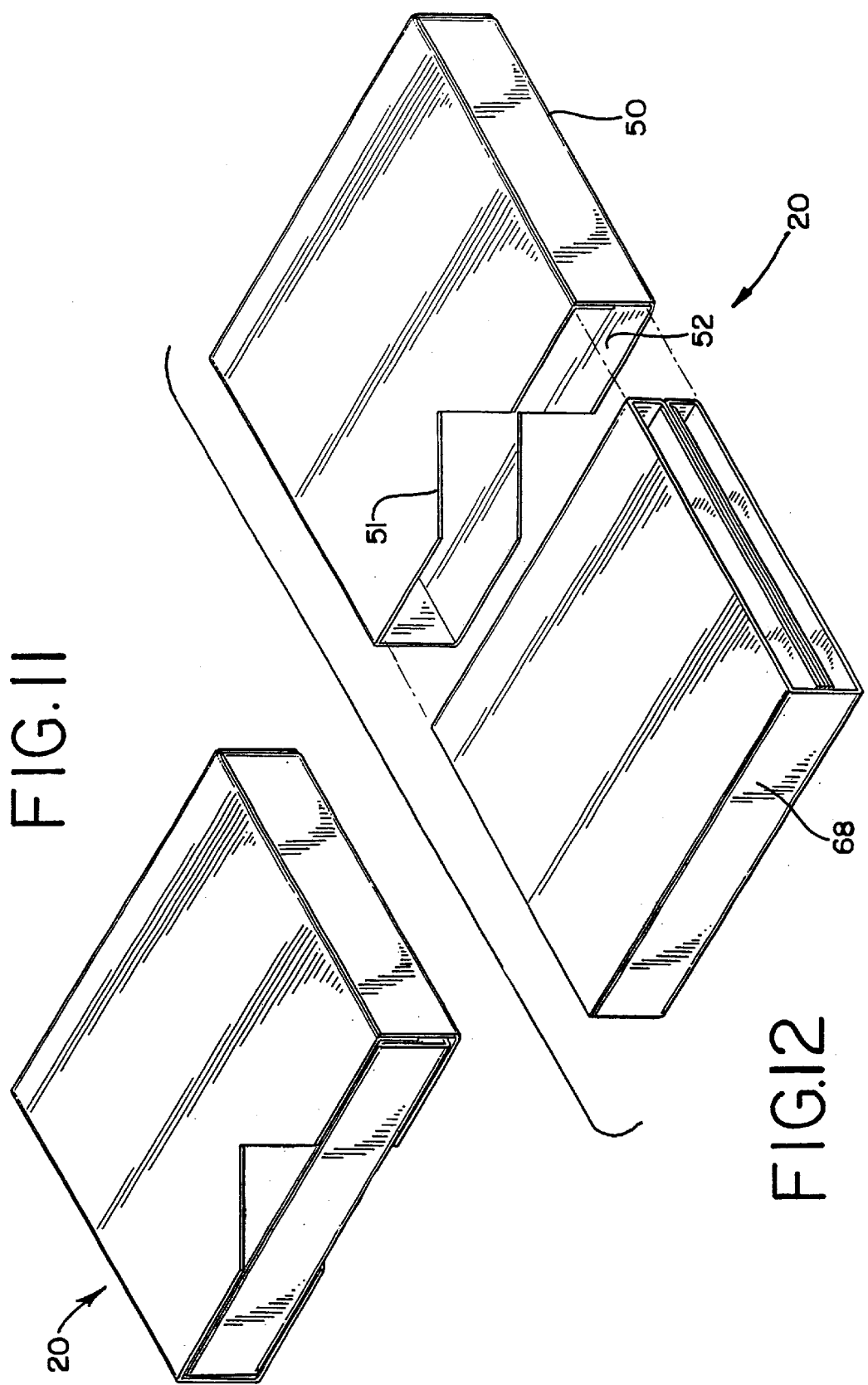

PHARMACEUTICAL PACKAGING SYSTEM

BACKGROUND OF THE INVENTION

The present invention relates generally to a packaging system for pharmaceutical products. More particularly, the present invention relates to a packaging system for storing and dispensing individual doses of medication on prescribed days.

The concept of a packaging system for storing and dispensing individual doses of medication is well known in the art. Some packaging systems include instructions on when to take the medication. The user must read and remember the instructions in order to know when to take the medication. The instructions typically set forth the times per day or week and the amount of days or weeks the user should take the medication. Since the instructions lack a reminder system, the user will often forget to take the medication. If the user forgets to take the medication, the user may have to take additional medication or the user may suffer health complications as a result.

Some packaging systems have indicia printed alongside the individual doses of medication to remind the user when to take the medication. The indicia may correspond to certain hours of the day, days of the week, and so forth. In the case of a bottle-type packaging system, the indicia are generally affixed to a member which is slidably or rotatably movable relative to a fixed index mark on the container. In the case of a blister-pack packaging system, wherein the medication is individually sealed within a blister, the indicia may be nothing more than printed information adjacent to each blister associating each dose of medication with a specified time period. The indicia may indicate the specific time when an individual dose of medication is to be taken.

Indicia are commonly used in packaging systems for birth control pills and one such device is known for dispensing aspirin tablets. The indicia used on such packaging systems are an integral part of the packaging system, and if a different schedule is desired, the packaging system is unusable for such a different schedule and a whole new packaging system along with new indicia must be prepared. Additionally, since the indicia are located within the packaging system, this type of reminder device is only somewhat effective for reminding users that have to take the medication on a periodic basis, since the user must look in the packaging system itself to remember when to take the medication. Moreover, this arrangement is effective only to the degree the user can remember to check the packaging system. If the user has to take the medication on an irregular basis or a lengthy periodic basis, such as a weekly basis, a reminder device with indicia printed in a packaging system will not be effective since the user is likely to forget to check the packaging system.

The dimensions of some packaging systems for medication cause the packaging systems to rest in a horizontal orientation parallel to the ground. However, a horizontal orientation is not as visible to a user as a vertical orientation that is normal to the ground. A packaging system which can rest in a vertical orientation would increase the user's awareness of the medication and aid the user in remembering to take the medication.

It is apparent from conventional packaging systems that there is a need for a packaging system which contains external reminders for effectively dispensing medication on an irregular basis; which contains external reminders for effectively dispensing medication on a lengthy periodic basis; which can rest in a vertical orientation; and which has a structure that prevents the loss of medication.

SUMMARY OF THE INVENTION

Briefly stated, the present invention is a packaging system for storing and dispensing individual doses of medication on prescribed days. The packaging system comprises a first sheet with individual doses of medication removably held thereon; a second sheet adapted to be folded over the first sheet; a plurality of labels held on either the first or second sheet, each label corresponding to one dose of medication, each of the labels being adapted to be removed from the first or second sheet and applied to a calendar to thereby serve as a reminder of the day on which the corresponding individual dose of medication is to be taken; and a sleeve with one open end for receiving the first and second sheets when in the folded state. The sleeve is designed to prevent the accidental loss of any dose of medication from the packaging system.

In one preferred embodiment of this invention, the packaging system has a spine upon which identification information may be placed in order to identify the packaging system. In one preferred embodiment of this invention, instructional information is placed on the spine or upon any of the sheets to instruct the user on how to operate the packaging system, how to dispense the doses of medication, how to take the doses of medication, or on any other matter related to packaging system. In one preferred embodiment of this invention, the packaging system further comprises a third sheet adapted to fold over the first or second sheet. In one preferred embodiment of this invention, the height of the sleeve is generally less than ten times the width of the sleeve. By limiting the height and width of the sleeve, the structure of the packaging system in such that the packaging system can rest in a vertical orientation. Third and/or fourth sheets can be added to the above packaging system along with any number and combination of spines.

As used in this specification, the terms "medication" and "doses of medication" are preferably medicinal substances used to treat humans or animals. The terms "medication" and "doses of medication" can be medication in dry tablet form, gel tablet form, capsule form, hardened pill form, liquid capsule form, or any other suitable form which medicinal substances can be stored known to those skilled in the art. Additionally, the terms "medication" and "doses of medication" can refer to vitamins, cosmetic substances, or any other similar substances.

The present invention has numerous advantages, a few of which are delineated hereafter. One advantage of the present invention is that the packaging system contains external reminders for effectively dispensing medication on an irregular basis.

A further advantage of the present invention is that the packaging system contains external reminders for effectively dispensing medication on a lengthy periodic basis.

Another advantage of the present invention is that the packaging system can rest in a vertical orientation.

Yet another advantage of the present invention is that the packaging system has a structure that prevents the loss of medication.

BRIEF DESCRIPTION OF THE DRAWINGS

The aforementioned and current features and objects of this invention will be better understood from the following detailed description in view of the drawings wherein:

FIG. 4 is a front view of a packaging system having a first, second, third, and fourth sheet, according to one preferred embodiment of this invention;

FIG. 5 is a front view of a packaging system having a first, second, third, and fourth sheet, according to another preferred embodiment of this invention;

FIG. 6 is a perspective view of a packaging system utilizing a cover sheet, a translucent sheet, a rupturable backing, and a first or fourth sheet to store and dispense individual doses of medication, according to one preferred embodiment of this invention;

FIG. 7 is a perspective view of a packaging system utilizing a cover sheet, a translucent sheet, a rupturable backing, and a first or fourth sheet to store and dispense individual doses of medication, according to another preferred embodiment of this invention;

FIG. 8 is a cross-sectional view of a blister as shown in FIG. 6, according to one preferred embodiment of this invention;

FIG. 9 is a cross-sectional view of a label as shown in FIG. 4, according to one preferred embodiment of this invention;

FIG. 10 is a front view of a sleeve of a packaging system, according to one preferred embodiment of this invention;

FIG. 11 is a perspective view of the packaging system, according to one preferred embodiment of this invention, wherein the packaging system is in a folded position and matingly engaged with a sleeve;

FIG. 12 is a perspective view of the packaging system shown in FIG. 11, wherein the packaging system is exiting the sleeve; and FIG. 13 is a perspective view of a partially unfolded packaging system, according to one preferred embodiment of this invention.

DETAILED DESCRIPTION OF THE INVENTION

The present invention will now be described more fully herein with reference to the accompanying drawings in which preferred embodiments of the invention are shown. This invention may, however, be embodied in many different forms and should not be construed as limited to the embodiments set forth herein. Rather, these embodiments are provided so that this disclosure will be thorough and complete, and will fully convey the scope of the invention to those skilled in the art. Like numbers refer to like elements throughout. As will be appreciated by one skilled in the art, the present invention may be embodied as a method, packaging system, or medication storage and dispensing product.

Figure 1:
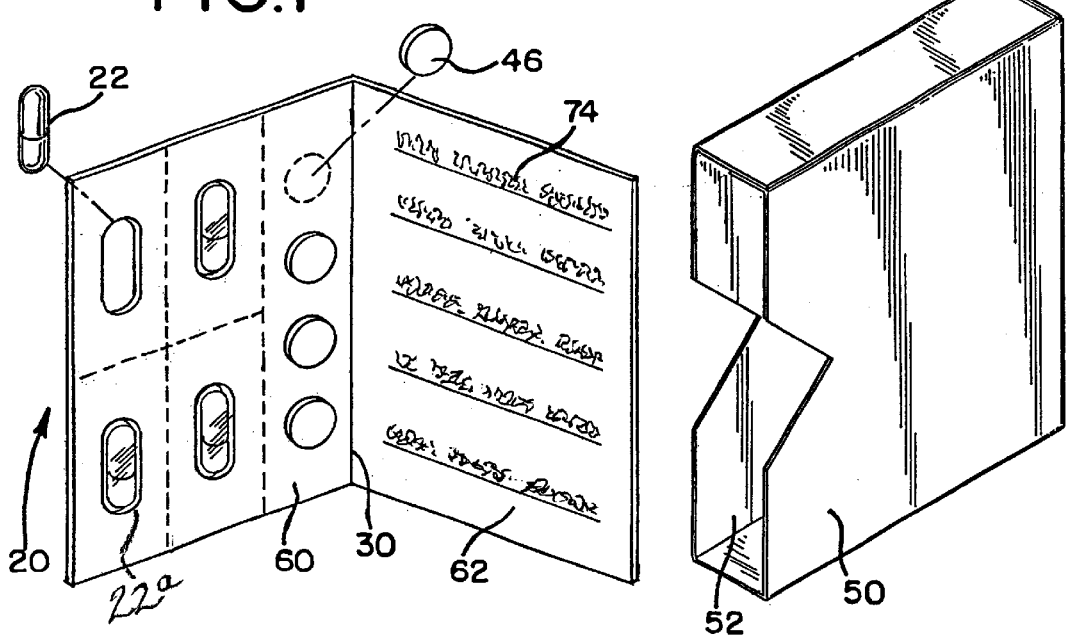
FIG. 1 is a perspective view of a packaging system for storing and dispensing individual doses of medication on prescribed days, according to one preferred embodiment of this invention.

FIG. 1 illustrates packaging system 20 for storing and dispensing individual doses of medication 22 on prescribed days. Packaging system 20 comprises first sheet 60, second sheet 62, labels 46, and sleeve 50. First sheet 60 has individual doses of medication 22 removably held thereon. First sheet 60 is preferably manufactured using a semi-rigid sheet of paper, however first sheet 60 can be manufactured using plastic or any other comparable material or combination of materials known to those skilled in the art. Individual doses of medication 22 can comprises any one of a variety of substances for treating a patient, aiding a patient, or supplementing a patient's diet, known to one of ordinary skill in the art, such as medications or vitamins. Individual doses of medication 22 are preferably medication in tablet form for treating humans or animals. However, individual doses of medication 22 can be medication in gel tablet form, capsule form, hardened pill form, liquid capsule form, or any other suitable form which medication can be stored known to those skilled in the art. Additionally, individual doses of medication 22 can be vitamins.

The Preferred Medication and Method of Making It

In one preferred embodiment of this invention, individual doses of medication 22 comprise the drug Fluoxetine. Fluoxetine (N-methyl-3-(p-trifluoromethylphenoxy)-3-phenylpropylamine) is an antidepressant drug which is disclosed, for example, in U.S. Pat. Nos. 4,314,081, 4,626,549, and 5,910,319 the entire disclosures of which are incorporated herein by reference.

Preferably, the medication is an enteric fluoxetine pellet comprising a) a core consisting of fluoxetine and one or more pharmaceutically acceptable excipients; b) an optional separating layer; c) an enteric layer comprising hydroxypropyl-methylcellulose acetate succinate (HPMCAS) and a pharmaceutically acceptable excipient; d) an optional finishing layer.

The Core

A preferred core for the pellet is prepared by applying a fluoxetine-containing layer to an inert core. Such inert cores are conventionally used in pharmaceutical science, and are readily purchased in all industrial countries. The most preferred core is one prepared from starch and sucrose, for use in confectionery as well as in pharmaceutical manufacturing. However, cores of any pharmaceutically acceptable excipient may be used, including, for example, microcrystalline cellulose, vegetable gums, waxes, and the like. The primary characteristic of the inert core is to be inert, with regard both to fluoxetine and the other excipients in the pellet and with regard to the patient who will ultimately ingest the pellet.

The size of the cores depends, of course, on the desired size of the pellet to be manufactured. In general, pellets can be as small as 0.1 mm, or as large as 2 mm. Preferred cores are from about 0.3 to about 0.8 mm, in order to provide finished pellets in the desired preferred size range of from about 0.5 to about 1.5 mm in diameter.

It is always preferred that the cores to be of a reasonably narrow particle size distribution, in order to improve the uniformity of the various coatings to be added and the homogeneity of the final product. For example, the cores may be specified as being of particle size ranges such as from 18 to 20 U.S. mesh, from 20 to 25 U.S. mesh, from 25 to 30 U.S. mesh, or from 30 to 35 U.S. mesh to obtain acceptable size distributions of various absolute sizes.

The amount of cores to be used obviously depends on the weights and thicknesses of the added layers; in general, the cores comprise from about 10 to about 70 percent of the product. More preferably, the charge of cores represents from about 15 to about 45 percent of the product.

When manufacture of the pellet begins with inert cores, the fluoxetine is coated on the cores to yield a final drug concentration of about 10 to about 25 percent of the product, in general. The amount of fluoxetine, of course, depends on the desired dose of the drug and the quantity of pellets desired to administer. The dose of fluoxetine is in the range of 20–100 mg (base equivalent), more usually 80–90 mg, and the usual number of pellets is that amount which is conveniently held in gelatin capsules. Comparison of the volume of gelatin capsules and the desired doses leads the pharmacist to the concentration range from about 15% to about 25% of fluoxetine in the present product.

Some attention must be given to the particle size of fluoxetine. The compound can precipitate in needle-like crystals which can be quite large. Coating cores with fluoxetine in the large needle-like form can be difficult, and it is advisable to mill or otherwise reduce the particle size of the fluoxetine to less than about 50 $\mu$m before using it in the present product and process.

A convenient manner of coating the cores with fluoxetine is the "powder coating" process where the cores are moistened with a sticky liquid or binder, fluoxetine is added as a powder, and the mixture is dried. Such a process is regularly carried out in the practice of industrial pharmacy, and suitable equipment is in daily use.

Such equipment is used in several steps of the present process, and is discussed in detail here. Historically, this process has been conducted in conventional coating pans similar to those employed in sugar coating processes. This process can be used to prepare pellets, but this equipment has less efficient air flow and drying capabilities which limits application rates and can result in longer processing times in order to minimize agglomerations.

Alternately, the present product could be made in fluidized bed equipment (using a rotary processor), or in rotating plate equipment such as the Freund CF-Granulator (Vector Corporation, Marion, Iowa). The rotating plate equipment typically consists of a cylinder, the bottom of which is a rotatable plate. Motion of the mass of particles to be coated is provided by friction of the mass between the stationary wall of the cylinder and the rotating bottom of it. Means can be provided to apply warm air to dry the mass, and liquids can be sprayed on the mass and balanced against the drying rate as in the fluidized bed case.

When a powder coating is applied, the mass of pellets, in the present case, is maintained in a sticky state, and the fluoxetine powder to be adhered to them, is added continuously or periodically and adheres to the sticky pellets. When all of the fluoxetine has been applied, the spray is stopped and the mass is allowed to dry in the air stream. It may be appropriate or convenient to add some inert powders to the fluoxetine.

Additional solids may be added to the layer with fluoxetine. These solids may be added to facilitate the coating process as needed to aid flow, reduce static charge, aid bulk buildup and form a smooth surface. Inert substances such as talc, kaolin, and titanium dioxide, lubricants such as magnesium stearate, finely divided silicon dioxide, crospovidone, and non-reducing sugars, e.g., sucrose, may be used. The amounts of such substances are in the range from about a few tenths of 1% of the product, up to about 20% of the product. Such solids should be of fine particle size, less than 50 $\mu$m, to produce a smooth surface.

The fluoxetine is made to adhere to the cores by spraying a pharmaceutical excipient which is sticky and adherent when it is wet, and dries to a strong, coherent film. Pharmaceutical scientists are aware of and conventionally use many such substances, most of them polymers. Such preferred polymers include hydroxypropylmethylcellulose, hydroxypropylcellulose and polyvinylpyrrolidone. Additional such substances include methylcellulose, carboxymethylcellulose, acacia and gelatin, for example. The amount of the adhering excipient is in the range from about 4% to about 12% of the product, and depends in large part on the amount of fluoxetine to be adhered to the core.

Fluoxetine may also be built up on the cores by spraying a slurry comprising fluoxetine suspended in a solution of the excipients of the fluoxetine layer, dissolved or suspended in sufficient water to make the slurry sprayable. Such a slurry may be milled through a machine adapted for grinding suspensions in order to reduce the particle size of fluoxetine. Grinding in suspension form is desirable because it avoids dust generation and containment problems which arise in grinding dry powder drugs. A preferred method for applying this suspension is in the classic pharmaceutical fluidized bed coating device, such as the Wurster column, which consists simply of a vertical cylinder with an air-permeable bottom and an upward spraying nozzle close above the bottom, or a downward-spraying nozzle mounted above the product mass. The cylinder is charged with particles to be coated, sufficient volume of air is drawn through the bottom of the cylinder to suspend the mass of particles, and the liquid to be applied is sprayed onto the mass. The temperature of the fluidizing air is balanced against the spray rate to maintain the mass of pellets or tablets at the desired level of moisture and stickiness while the coating is built up.

On the other hand, the core may comprise a monolithic particle in which the fluoxetine is incorporated. Such cores may be prepared by the granulation techniques which are wide spread in pharmaceutical science, particularly in the preparation of granular material for compressed tablets. The particle size of the cores is too small for preparation by compression techniques, but the cores may be prepared by mixing the fluoxetine into a mass of pharmaceutical excipients, moistening the mass with water or a solvent, drying, and breaking the mass into sized particles in the same size range as described above for the inert cores. This can be accomplished via the process of extrusion and marumerization.

The core for the pellet can also be prepared by mixing fluoxetine with conventional pharmaceutical ingredients to obtain the desired concentration and forming the mixture into cores of the desired size by conventional procedures or by the process of R. E. Sparks, et al., U.S. Pat. Nos. 5,019,302 and 5,100,592, incorporated by reference herein.

Separating Layer

The separating layer between the fluoxetine-containing core and the enteric layer is not required, but is a preferred feature of the formulation. The functions of the separating layer, if required, are to provide a smooth base for the application of the enteric layer, to prolong the pellet's resistance to acid conditions, and to improve stability by inhibiting any interaction between the drug and the enteric polymer in the enteric layer.

The smoothing function of the separating layer is purely mechanical, the objective of which is to improve the coverage of the enteric layer and to avoid thin spots in it caused by bumps and irregularities on the core. Accordingly, the more smooth and free of irregularities the core can be made, the less material is needed in the separating layer, and the need for the smoothing characteristic of the separating layer may be avoided entirely when the fluoxetine is of extremely fine particle size and the core is made as truly spherical as possible.

It has been found that when a pharmaceutically acceptable non-reducing sugar is added to the separating layer, the pellet's resistance to acid conditions is markedly and surprisingly increased. Accordingly, such a sugar may be included in the separating layer applied to the cores, either as a powdered mixture, or dissolved as part of the sprayed-on liquid. A sugar-containing separating layer can reduce the quantity of enteric polymer required to obtain a given level of acid resistance. It therefore considerably reduces the expense of the present formulated product. Use of less enteric polymer reduces both the materials cost and processing time, and also reduces the amount of polymer available to react with fluoxetine. The inhibition of any core/enteric layer interaction is mechanical. The separating layer physically keeps the components in the core and enteric layers from coming into direct contact with each other. In some cases, the separating layer can also act as a diffusional barrier to migrating core or enteric layer components dissolved in product moisture. The separating layer can also be used as a light barrier by opacifying it with agents such as titanium dioxide, iron oxides and the like.

In general, the separating layer is composed of coherent or polymeric materials, and finely powdered solid excipients which constitute fillers. When a sugar is used in the separating layer, it is applied in the form of an aqueous solution and constitutes part of or the whole of the coherent material which sticks the separating layer together. In addition to or instead of the sugar, a polymeric material may also be used in the separating layer. For example, substances such as hydroxypropylmethylcellulose, polyvinylpyrrolidone, hydroxypropylcellulose and the like may be used in small amounts to increase the adherence and coherence of the separating layer.

It is further advisable to use a filler excipient in the separating layer to increase the smoothness and solidity of the layer. Substances such as finely powdered talc, silicon dioxide and the like are universally accepted as pharmaceutical excipients and may be added as is convenient in the circumstances to fill and smooth the separating layer.

In general, the amount of sugar in the separating layer may be in the range of from about 2% to about 10% of the product, when a sugar is used at all, and the amount of polymeric or other sticky material may be in the range of from about 0.1 to about 5%. The amount of filler, such as talc, should be in the range of from about 5 to about 15%, based on final product weight.

The separating layer may be applied by spraying aqueous solutions of the sugar or polymeric material, and dusting in the filler as described in the preparation of a fluoxetine layer. The smoothness and homogeneity of the separating layer can be improved, however, if the filler is thoroughly dispersed as a suspension in the solution of sugar and/or polymeric material, and the suspension is sprayed on the core and dried, using equipment as described above in the preparation of cores with fluoxetine layers.

Enteric Layer

The enteric layer is comprised of an enteric polymer, which must be chosen for compatibility with fluoxetine as discussed above. The polymer must have only a small number of carboxylic acid groups per unit weight or repeating unit of the polymer. The preferred enteric polymer is hydroxypropylmethylcellulose acetate succinate (HPMCAS), which product is defined as containing not less than 4% and not more than 28% of succinoyl groups, which are the only free carboxylic groups in the compound. See Japanese Standards of Pharmaceutical Ingredients 1991, page 1216–21, Standard No. 19026. HPMCAS is available from Shin-Etsu Chemical Co., Ltd., Tokyo, Japan, under the trademark AQOAT. It is available in two particle size grades and three molecular weight ranges. The L grade, having number average molecular weight of 93,000, is used in the present examples but other grades are expected to be usable.

Enteric polymers may be applied as coatings from aqueous suspensions, from solutions in aqueous or organic solvents, or as a powder. Application from organic solvents is presently not at all favored in the pharmaceutical industry, because of the cost of the solvent and the difficulty in either disposing of solvent vapors or recovering the evaporated solvent. Accordingly, no detailed discussion of application of the enteric layer from organic solvents will be given here, but the pharmaceutical scientist will recognize that such application is entirely possible if circumstances favor it.

The enteric polymer can also be applied according to a method described by Shin-Etsu Chemical Co. Ltd. (Obara, et al., Poster PT6115, AAPS Annual Meeting, Seattle, Wash., Oct. 27–31, 1996). When the enteric polymer is applied as a powder the enteric polymer is added directly in the solid state to the tablets or pellets while plasticizer is sprayed onto the tablets or pellets simultaneously. The deposit of solid enteric particles is then turned into a film by curing. The curing is done by spraying the coated tablets or pellets with a small amount of water and then heating the tablets or pellets for a short time. This method of enteric coating application can be performed employing the same type of equipment as described above in the preparation of cores with fluoxetine layers When the enteric polymer is applied as an aqueous suspension, a problem in obtaining a uniform, coherent film often results. It is very advisable, accordingly, to purchase a fine particle grade or grind the particles of polymer to an extremely small size before application. It is possible either to grind the dry polymer, as in an air-impaction mill or to prepare the suspension and grind the polymer in slurry form. Slurry grinding is generally preferable, particularly since it can be used also to grind the filler portion of the enteric layer in the same step. It is advisable to reduce the average particle size of the enteric polymer to the range from about 1 $\mu$m to about 5 $\mu$m, preferably no larger than 3 $\mu$m.

When the enteric polymer is applied in the form of a suspension, it is important to assure that the suspension remains homogeneous, and that conditions which favor the agglomeration of the polymer do not occur. Such precautions include maintaining the suspension in a gently stirred condition, but not stirring so vigorously as to create foam, and assuring that the suspension does not stand still in eddies in nozzle bodies, for example, or in over-large delivery tubing. Frequently polymers in suspension form will agglomerate if the suspension becomes too warm, and the critical temperature may be as low as 30° C. in individual cases. Since spray nozzles and tubing are exposed to hot air in the usual fluid bed type equipment, care must be taken to assure that the suspension is kept moving briskly through the equipment to cool the tubing and nozzle. When HPMCAS is used, in particular, it is advisable to cool the suspension below 20° C. before application, to cool the tubing and nozzle by pumping a little cold water through them before beginning to pump the suspension, and to use supply tubing with as small a diameter as the spray rate will allow so that the suspension can be kept moving rapidly in the tubing.

It is preferred, however, to apply the enteric polymer as an aqueous solution whenever it is possible to do so. In the case of HPMCAS, dissolution of the polymer can be obtained by neutralizing the polymer, preferably with ammonia. Neutralization of the polymer may be obtained merely by adding ammonia, preferably in the form of aqueous ammonium hydroxide to a suspension of the polymer in water; complete neutralization results in complete dissolution of the polymer at about pH 5.7–5.9. Good results are also obtained when the polymer is partially neutralized, by adding less than the equivalent amount of ammonia. In such case, the polymer which has not been neutralized remains in suspended form, suspended in a solution of neutralized polymer. As noted earlier, it is obviously important to control the particle size of the polymer when such a process is to be used. Use of neutralized polymer more readily provides a smooth, coherent enteric layer than when a suspended polymer is used, and use of partially neutralized polymer provides intermediate degrees of smoothness and coherency. Particularly when the enteric layer is applied over a very smooth separating layer, excellent results may be obtained from partially neutralized enteric polymer.

The extent of neutralization may be varied over a range without adversely affecting results or ease of operation. For example, operation with from about 25% to about 100% neutralization is preferred. Another preferred condition is from about 45% to about 100% neutralization, and another preferred condition is from about 65% to about 100%. Still another preferred manner of neutralization is from about 25% to about 65% neutralized. It is found, however, that the enteric polymer in the resulting product, after drying, is neutralized to a lesser extent than when applied. When neutralized or partially neutralized HPMCAS is applied, the HPMCAS in the final product is from about 0% to about 25% neutralized, more preferably from about 0% to about 15% neutralized.

Most enteric polymers require the addition of a plasticizer for best results. In the case of HPMCAS, the preferred plasticizer is triethyl citrate, used in an amount up to about 15%–30% of the amount of enteric polymer in aqueous suspension application. When a neutralized HPMCAS is employed, lower levels or no plasticizer may be required.

Minor ingredients, such as antifoam, suspending agents when the polymer is in suspended form, and surfactants to assist in smoothing the film are also commonly used. For example, silicone anti-foams, surfactants such as polysorbate 80, sodium lauryl sulfate and the like and suspending agents such as carboxymethylcellulose, vegetable gums and the like may commonly be used at amounts in the general range up to 1% of the product.

Usually, an enteric layer is filled with a powdered excipient such as talc, glyceryl monostearate or hydrated silicon dioxide to build up the thickness of the layer, to strengthen it, to reduce static charge, and to reduce particle cohesion. Amounts of such solids in the range of from about 1% to about 10% of the final product may be added to the enteric polymer mixture, while the amount of enteric polymer itself is usually in the range from about 5% to about 25%, more preferably, from about 10% to about 20%.

Application of the enteric layer to the pellets follows the same general procedure previously discussed, using fluid bed type equipment with simultaneous spraying of enteric polymer solution or suspension and warm air drying. Temperature of the drying air and the temperature of the circulating mass of pellets should be kept in the ranges advised by the manufacturer of the enteric polymer.

Finishing Layer

A finishing layer over the enteric layer is not necessary in every case, but frequently improves the elegance of the product and its handling, storage and machinability and may provide further benefits as well. The simplest finishing layer is simply a small amount, about less than 1% of an anti-static ingredient such as talc or silicon dioxide, simply dusted on the surface of the pellets. Another simple finishing layer is a small amount, about 1%, of a wax such as beeswax melted onto the circulating mass of pellets to further smooth the pellets, reduce static charge, prevent any tendency for pellets to stick together, and increase the hydrophobicity of the surface.

More complex finishing layers may constitute a final sprayed-on layer of ingredients. For example, a thin layer of polymeric material such as hydroxypropylmethylcellulose, polyvinylpyrrolidone and the like, in an amount such as from about 2% up to about 10%, may be applied. The polymeric material may also carry a suspension of an opacifier, a bulking agent such as talc, or a coloring material, particularly an opaque finely divided color agent such as red or yellow iron oxide. Such a layer quickly dissolves away in the stomach, leaving the enteric layer to protect the fluoxetine, but provides an added measure of pharmaceutical elegance and protection from mechanical damage to the product.

Finishing layers to be applied to the present product are of essentially the same types commonly used in pharmaceutical science to smooth, seal and color enteric products, and may be formulated and applied in the usual manners.

In the most preferred embodiment, the Fluoxetine capsules are made according to the following formulation:

| Bill of Materials | |
|---|---:|
| Cores | |
| Sucrose-starch nonpareils, 30–35 mesh | 100–150 mg |
| Fluoxetine layer | |
| Fluoxetine hydrochloride | 100.5–100.8 mg |
| Sucrose | 20–30 mg |
| Hydroxypropylmethylcellulose | 10–15 mg |
| Separating layer | |
| Hydroxypropylmethylcellulose | 4–12 mg |
| Sucrose | 15–35 mg |
| Talc, 500 mesh | 25–60 mg |
| Enteric layer | |
| HPMCAS-LF | 60–90 mg |
| Triethyl citrate | 10–20 mg |
| Talc, 500 mesh | 15–25 mg |
| Finishing layer | |
| Color mixture white (HPMC + titanium dioxide) | 35–55 mg |
| HPMC | 5–15 mg |
| Talc | Trace |

In another preferred embodiment of this invention, at least one individual dose of medication 22 comprises a substance that differs from a substance comprised by a second individual dose of medication 22a. For example, in this embodiment, packaging system 20 may comprise a first individual dose of medication 22 that comprises the drug Fluoxetine and a second individual dose of medication 22a that comprises a second drug. In this same embodiment, a first individual dose of medication 22 comprises a first substance located on one sheet of packaging system 20, such as first sheet 60, and a second individual dose of medication 22a comprises a second substance is located on another sheet of packaging system 20, such as second sheet 62 or third sheet 64.

Individual doses of medication 22 are removably attached to first sheet 60 in any one of a number of ways. For example, in one preferred embodiment of this invention, individual doses of medication 22 are stored in blister-pack arrangement 34, as illustrated in FIGS. 4–7. In this embodiment, individual doses of medication 22 are removed from first sheet 60 by pushing individual doses of medication 22 through rupturable backing 42 which seals each individual blister 38 in blister-pack arrangement 34.

Second sheet 62 is adapted to be folded over first sheet 60. Second sheet 62 is preferably manufactured from the same or similar materials as first sheet 60, however second sheet 62 may be manufactured from any other comparable material or combination of materials known to those skilled in the art. Second sheet 62 is adapted to fold over first sheet 60 so that second sheet 62 can serve as a shield to protect individual doses of medication 22 attached to first sheet 60. Second sheet 62 an be adapted to fold over first sheet 60 in any one of a number of ways. For example, in one preferred embodiment of this invention second sheet 62 is adapted to fold over first sheet 60 by forming second sheet 62 on the same sheet of material as first sheet 60 and inserting a scored edge 30 in between second sheet 62 and first sheet 60. Scored edge 30 is a groove which is formed by placing an impression or indentation along the surface of first sheet 60 and second sheet 62. The impression or indentation aids in folding second sheet 62 over first sheet 60. Second sheet 62 can also be formed on a sheet of material separate and apart from first sheet 60 and then attached to first sheet 60 using a ring binder, glue, staple, or any other means known to those skilled in the art which can attach two sheets of material together.

Figure 2:
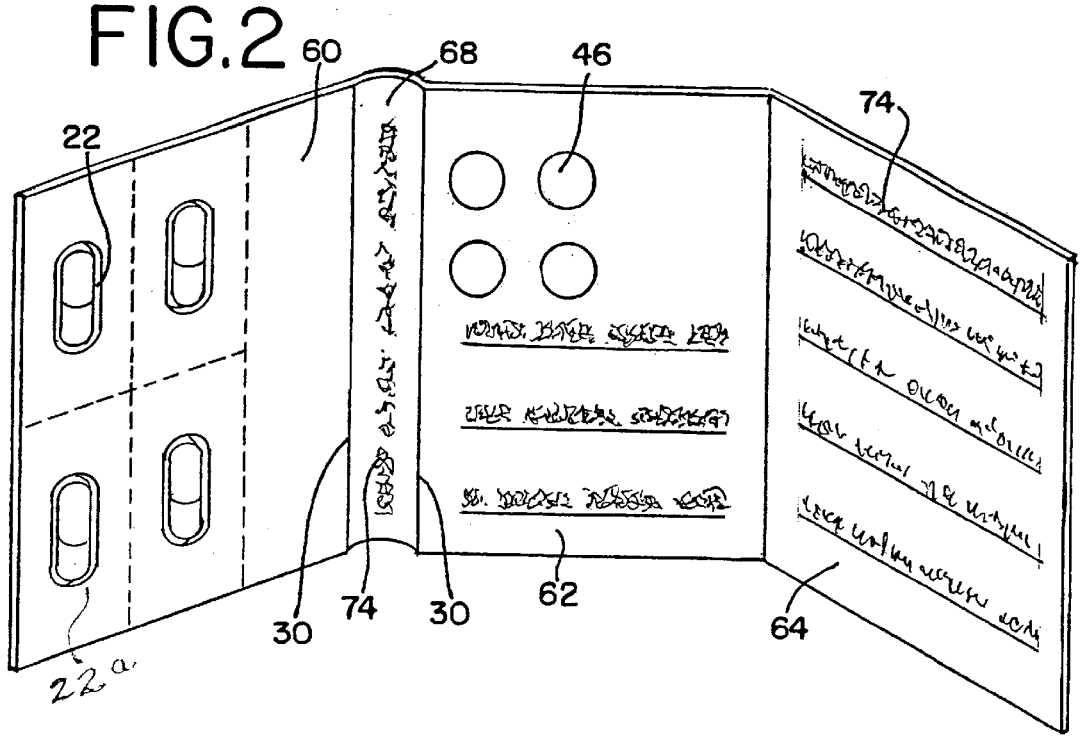
FIG. 2 is a front view of a packaging system having a first, second, and third sheet, according to another preferred embodiment of this invention.

In one preferred embodiment of this invention, the plurality of labels 46 are held on either first sheet 60 or second sheet 62, as illustrated in FIGS. 1–2. Labels 46 are adapted to be removed from the first sheet 60 or second sheet 62 and applied to a calendar, day planner book, or any surface which serves to reminder a user of a certain task. By placing label 46 on a calendar, day planner book, or any surface which serves to reminder a user of a certain task, the user can be reminded when to take doses of medication 22, without having to look in packaging system 20, thus reducing the chance that the user will forget to take doses of medication 22 on prescribed days.

In one preferred embodiment of this invention, labels 46 are manufactured from a sheet of material such as paper, plastic, or any other suitable material known to those skilled in the art which can be removably affixed to a sheet of material such as first sheet 60, as illustrated in FIG. 9. Label 46 overlies primary adhesive layer 47. Primary adhesive layer 47 is fixedly attached with respect to label 46. Primary adhesive layer 47 overlies non-adhesive layer 48 and is removably attached to non-adhesive layer 48. Primary adhesive layer 47 is comprised of an adhesive material such as glue, which can be removably attached to non-adhesive layer 48 but fixedly attached to label 46. Non-adhesive layer 48 is fixedly attached to first sheet 60 or second sheet 62. In one preferred embodiment of this invention, a secondary adhesive layer 49 is used to fixedly attach non-adhesive layer 48 to first sheet 60 or second sheet 62. By using non-adhesive layer 48, label 46 can be easily removed from first sheet 60 and attached to another surface. While in the above embodiments, label 46 is sheet of material which adheres to first sheet 60 or second sheet 62 using a primary adhesive layer 47, labels 46 can be any structure which can be removably attached to first sheet 60 or second sheet 62. For example, labels 46 could be a magnetic strip which is held onto first sheet 60 or second sheet 62 with a magnetic force. In one preferred embodiment of this invention, label 46 is manufactured using Velcro.

Each label 46 corresponds to one dose of medication 22. Therefore, for every dose of medication 22 in packaging system 20 there should be at least one label 46. This way the user can remove at least one label 46 for each dose of medication 22. Additional labels 46 can be held on first sheet 60 or second sheet 62. These additional labels 46 can be placed in additional locations, such as a second calendar, to serve as additional reminders to the user. By removing one label 46 for each dose of medication 22, and placing label 46 on a calendar or other similar surface which serves to reminder a user of a certain task, packaging system 20 serves to remind the user of the day on which the corresponding individual dose of medication 22 is to be taken. In one preferred embodiment of this invention, individual doses of medication 22 are arranged in a pattern and the plurality of labels 46 are arranged in a corresponding pattern, as illustrated in FIGS. 4–5. By arranging the plurality of labels 46 in the same pattern as doses of medication 22 the user can more easily associate each label 46 with each dose of medication 22. While in the above embodiments, the plurality of labels 46 are held on either first sheet 60 or second sheet 62, the plurality of labels 46 can be held on any sheet within packaging system 20, such as third sheet 64 and/or fourth sheet 66.

Sleeve 50 forms one open end 52. Sleeve 50 is preferably manufactured from the same or similar materials as first sheet 60, however sleeve 50 may be manufactured from any other comparable material or combination of materials known to those skilled in the art. Open end 52 and sleeve 50 engage the first sheet 60 and second sheet 62 when in the folded state. Preferably, open end 52 and sleeve 50 matingly engage with first sheet 60 and second sheet 62. By forming a relatively tight clearance between sleeve 50, first sheet 60, and second sheet 62, first sheet 60 and second sheet 62 can rest securely within sleeve 50 without significant wobble. In another preferred embodiment of this invention, sleeve 50 includes at least one notch 51 adjacent open end 52 for facilitating removal of the first sheet 60 and second sheet 62 from sleeve 50.

Sleeve 50 is designed to protect first sheet 60 and second sheet 62 when in the folded states. Sleeve 50 is also designed to prevent the accidental loss of any dose of medication 22 from packaging system 20. Sleeve 50 can be formed by connecting two sheets of paper, each sheet of paper having four edges. The sheets of paper are connected at three edges, forming sleeve 50 with one open end 52. In one preferred embodiment, sleeve 50 has base 78 opposed to top 82, and three sides 80 spanning from base 78 to top 82, as illustrated in FIG. 10. In another preferred embodiment of this invention, sleeve 50 is designed to stand in an upright position, normal to the ground. In the upright position, base 78 of sleeve 50 is parallel to the ground and sides 80 of sleeve 50 are normal to the ground. The height of sleeve 50 is defined as the distance from base 78 to top 82, and the width of sleeve 50 is defined as the width of base 78, as illustrated in FIG. 10. If the width of base 78 is not consistent, then the maximum width of base 78 is the width of sleeve 50. Sleeve 50 must have a width great enough so that sleeve 50 can rest in an upright position. Preferably, the height of sleeve 50 is generally less than ten times the width of the sleeve 50, allowing sleeve 50 to comfortably stand in an upright position.

While the above embodiments have been described with respect to first sheet 60 and second sheet 62, as will be appreciated by those of skill in the art, the same embodiments may comprise additional sheets attached to first sheet 60, second sheet 62 or both first sheet 60 and second sheet 62. For example, in one preferred embodiment of this invention, spine 68 is formed between first sheet 60 and second sheet 62, as illustrated in FIG. 2. Spine 68 is adapted to act as barrier between first sheet 60 and second sheet 62. Spine 68 also allows for a tighter clearance between sleeve 50, first sheet 60, and second sheet 62. Spine 68 can be adapted to act as barrier between first sheet 60 and second sheet 62 in any one of a number of ways. For example, in one preferred embodiment of this invention, spine 68 is adapted to act as barrier between first sheet 60 and second sheet 62 by forming spine 68 on the same sheet of material as first sheet 60 and second sheet 62, and inserting one scored edge 30 in between first sheet 60 and spine 68 and a second scored edge 30 in between second sheet 62 and spine 68. In another preferred embodiment of this invention, spine 68 bears identification information 76 relating to the doses of medication 22. Identification information 76 identifies the type of medication stored and dispensed within packaging system 20. As will be appreciated by those of skill in the art, spine 68 can bear any type of information, including instructional information 74 which instructs the user on how to operate packaging system 20, how to dispense doses of medication 22, how to take doses of medication 22, or on any other mater related to packaging system 20. Additionally, spine 68 can be placed in between any two sheets such as first sheet 60 and second sheet 62, second sheet 62 and third sheet 64, and third sheet 64 and fourth sheet 66, as illustrated in FIG. 5.

Figure 3:
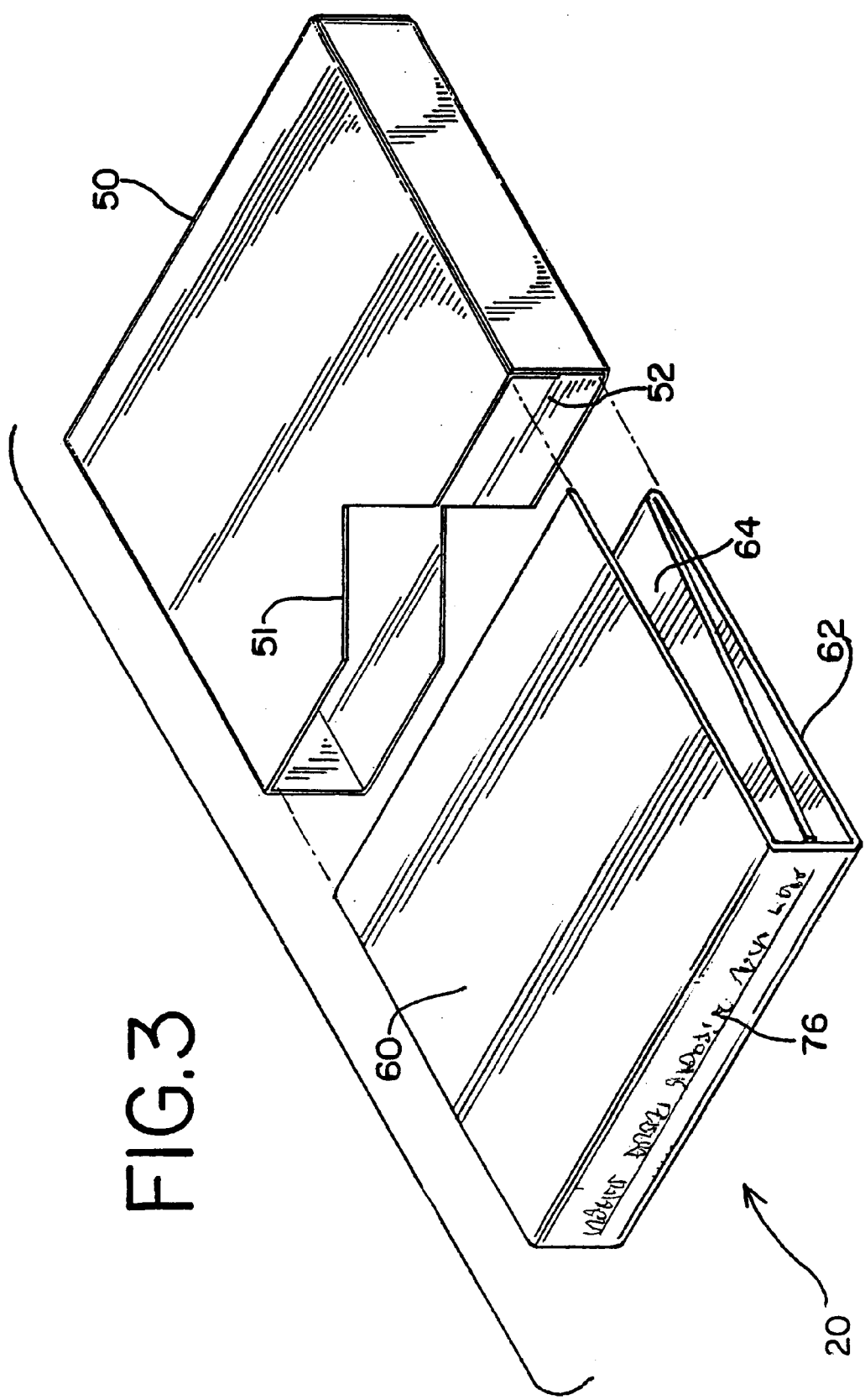
FIG. 3 is a perspective view of the packaging system shown in FIG. 2, wherein the packaging system is in a folded position and entering a sleeve.

In one preferred embodiment of this invention, packaging system 20 comprises third sheet 64 adapted to fold over the second sheet 62 or first sheet 60, as illustrated in FIGS. 2–3. Third sheet 64 is preferably manufactured from the same or similar materials as first sheet 60, however third sheet 64 may be manufactured from any other comparable material or combination of materials known to those skilled in the art. If third sheet 64 is adapted to fold over first sheet 60, third sheet 64 can serve as a shield to protect individual doses of medication 22 attached to first sheet 60. Third sheet 64 can be adapted to fold over first sheet 60 much the same way second sheet 62 is adapted to fold over first sheet 60, as described above. In one preferred embodiment of this invention, third sheet 64 is attached to second sheet 62, as illustrated in FIG. 2. In this configuration, third sheet 64 can be adapted to fold over second sheet 62 or first sheet 60. In one preferred embodiment of this invention, third sheet 64 is disposed between the first sheet 60 and second sheet 62. In this configuration, second sheet 62 or first sheet 60 can be adapted to fold over third sheet 64.

In one preferred embodiment of this invention, packaging system 20 comprises fourth sheet 66 adapted to fold over the third sheet 64. Fourth sheet 66 is preferably manufactured from the same or similar materials as first sheet 60, however fourth sheet 66 may be manufactured from any other comparable material or combination of materials known to those skilled in the art. Fourth sheet 66 can be adapted to fold over third sheet 64 in much the same way second sheet 62 is adapted to fold over first sheet 60, as described above. In one preferred embodiment of this invention, individual doses of medication 22 are removably held on fourth sheet 66. In another preferred embodiment of this invention, individual doses of medication 22 are removably held on fourth sheet 66 and first sheet 60. By holding individual doses of medication 22 on the fourth sheet 66 and first sheet 60, it becomes much more difficult for doses of medication 22 to accidentally escape through rupturable backing 42 when the packaging system 20 is in the folded position, since the fourth sheet 66 is pressed against the first sheet 60. Similarly in a three sheet configuration, if the third sheet 64 is folded over the first sheet 60, it becomes much more difficult for doses of medication 22 to accidentally escape through rupturable backing 42 since the third sheet 64 is pressed against first sheet 60.

While the above embodiments have individual doses of medication 22 removably held on the first sheet 60 and the fourth sheet 66, individual doses of medication 22 can be held on any one of first sheet 60, second sheet 62, third sheet 64, or fourth sheet 66, as will be appreciated by those of skill in the art. Additionally, instructional information 74 and identification information 76 can be placed anywhere on packaging system 20 such as on first sheet 60, second sheet 62, third sheet 64, fourth sheet 66, spine 68, or sleeve 50. In one preferred embodiment of this invention, identification information 76 is placed on spine 68 and is visible when sleeve 50 is matingly engaged with any one of first sheet 60, second sheet 62, third sheet 64, and fourth sheet 66.

In one preferred embodiment according to this invention each individual dose of medication 22 has a unique mark 44A associated therewith and each label 46 also has a unique mark 44B associate therewith. Unique marks 44A and 44B are unique only in the sense that no unique mark 44B for each label 46 corresponds with any other unique mark 44B for each label 46, and no unique mark 44A for each dose of medication 22 corresponds with any other unique mark 44A for each dose of medication 22. However, each label 46 bears a unique mark 44B, which unique mark 44B corresponds with one unique mark 44A associated with doses of medication 22. The unique marks 44A associated with doses of medication 22 and the unique marks 44B associated with labels 46 can be any one of a variety of marks such as matching number, matching letters, matching symbols, or even matching colors or shapes. In another preferred embodiment of this invention, individual doses of medication 22 are arranged in a pattern and the plurality of labels 46 are arranged in a corresponding pattern, wherein unique mark 44B on labels 46 is situated in generally the same location in the pattern as the one unique mark 44A associated with doses of medication 22. By positioning the unique mark 44A and 44B in the same location, and by using corresponding marks on labels 46 as on doses of medication 22, each dose of medication 22 can more easily be associated with one unique mark 44B.

In one preferred embodiment of this invention, doses of medication 22 are stored in a blister-pack arrangement 34, as illustrated in FIGS. 6–8. Blister pack-arrangement 34 comprises translucent sheet 36 and rupturable backing 42, and is mounted atop first sheet 60. First sheet 60 forms a plurality of cutouts 54, each cutout 54 defining an opening 28 having an area large enough for one dose of medication 22 to go through. Cutouts 54 can be perforated, as illustrated in FIG. 6 or cutouts 54 can be non-perforated, as illustrated in FIG. 7. Translucent sheet 36 is placed over a portion of first sheet 60, essentially overlapping first sheet 60. Translucent sheet 36 forms a plurality of blisters 38 and is preferably manufactured from clear plastic, however translucent sheet 36 can be manufactured from any other comparable material or combination of materials known to those skilled in the art. Preferably, plurality of blisters 38 are arranged in a pattern on translucent sheet 36, so as to more easily associate each label 46 with each dose of medication 22. However, plurality of blisters 38 does not have to be arranged in a pattern. Each blister 38 has a hollow cavity 40 upon which one dose of medication 22 is stored. Rupturable backing 42 seals the hollow cavity 40 so as to prevent contamination of dose of medication 22, each rupturable backing 42 positioned to overlap each opening 28. Rupturable backing 42 is preferably manufactured using a flexible, rupturable material such as a thin metallic sheet, however rupturable backing 42 can be manufactured using plastic or any other comparable material or combination of materials known to those skilled in the art. Rupturable backing 42 is sandwiched in between translucent sheet 36 and first sheet 60. When a user wishes to take dose of medication 22 from packaging system 20, all the user must do is apply pressure against blister 38 causing dose of medication 22 to break rupturable backing 42 and exit packaging system 20 through opening 28.

In another preferred embodiment of this invention, packaging system 20 comprises cover sheet 53, as illustrated in FIGS. 6–7. Cover sheet 53 forms a plurality of cutouts 54 which generally conform to the shape of the plurality of blisters 38. Cover sheet 53 overlaps translucent sheet 36, securing translucent sheet 36 to first sheet 60. While the above blister-pack arrangement 34 has been described with respect to first sheet 60, as will be appreciated by those of skill in the art, the same blister-pack arrangement 34 may be described with respect to second sheet 62, third sheet 64, and fourth sheet 66.

In one preferred embodiment of this invention, blister-pack arrangement 34 is mounted atop first sheet 60 and fourth sheet 66, as illustrated in FIGS. 4–5 and FIG. 13. Second sheet 62 is adapted to fold over to first sheet 60 and third sheet 64 is adapted to fold over fourth sheet 66, as illustrated in FIG. 13. By adapting second sheet 62 to fold over to first sheet 60 and third sheet 64 to fold over fourth sheet 66, first sheet 60 presses against fourth sheet 66 when in the folded position. This arrangement prevents doses of medication 22 from accidentally escaping through opening 28 when blister-pack arrangement 34 is in the folded position.

EXAMPLES

The following Examples set out the preparation of a number of different enteric Fluoxetine granules. The Examples are intended to further enlighten the reader about the present enteric pellets and their methods of manufacture; additional variations within the concept of the invention will be clear to the pharmaceutical scientist and their preparation will be within the scientist's competence.

For each example, a bill of materials will first be given, which will be expressed in terms of the amount of each ingredient used to prepare a single unit dose of the granules. Following the bill of materials, the process will be described, giving the equipment and the batch size used in the various stages of manufacture.

Example 1

90 mg Fluoxetine base/capsule

Bill of Materials

| | |
|---|---:|
| Cores | |
| Sucrose-starch nonpareils, 30–35 mesh | 134.15 mg |
| Fluoxetine layer | |
| Fluoxetine | 100.58 mg |
| Sucrose | 25.72 mg |
| Hydroxypropylmethylcellulose | 12.89 mg |
| Separating layer | |
| Hydroxypropylmethylcellulose | 9.45 mg |
| Sucrose | 28.24 mg |
| Talc, 500 mesh | 50.21 mg |
| Enteric layer | |
| HPMCAS-LF | 65.66 mg |
| Triethyl citrate | 13.14 mg |
| Talc, 500 mesh | 19.66 mg |
| Finishing Layer | |
| Color mixture white (HPMC + titanium dioxide) | 43.02 mg |
| HPMC | 10.78 mg |
| Talc | Trace |
| | 513.50 mg |

The fluoxetine layer was built up by suspending fluoxetine hydrochloride 25% w/w in a binder solution consisting of 6.4% w/w sucrose and 3.2% w/w hydroxypropyl methylcellulose (HPMC). The resulting suspension was then passed through a Coball Mill (Fryma Mashinen AG, Rheinfelden, Switzerland) model MS-12 to reduce the particle size of the bulk drug. The milled suspension was applied to 1.5 kg of sucrose starch non-pareils in a fluid bed dryer which had been fitted with a Wurster column. Upon completing the application of the desired quantity of fluoxetine hydrochloride suspension, the fluoxetine core pellets were completely dried in the fluid bed dryer.

The separating layer which consisted of talc 1 2% w/w, sucrose 6.75% w/w and hydroxypropyl methylcellulose 2.25% w/w was then applied as an aqueous suspension to the fluoxetine core pellets. Upon completing the application of the desired quantity of suspension, the pellets were completely dried in the fluid bed dryer.

The enteric coating aqueous suspension consisted of hydroxypropyl methylcellulose acetate succinate type LF 6% w/w, talc 1.8% w/w, triethyl citrate 1.2% w/w which was fully neutralized by the addition of 0.47% w/w ammonium hydroxide. This enteric coating suspension was applied to the fluoxetine separation layer coated pellets. Upon completing the application of the desired quantity of enteric coating suspension, the pellets were completely dried in the fluid bed dryer and a small quantity of talc was added to reduce static charge.

A finishing layer was then applied which consisted of color mixture white (comprised of titanium dioxide and hydroxypropyl methylcellulose) 8% w/w and hydroxypropyl methylcellulose 2% w/w. Upon completing the application of the desired quantity of color coating suspension, the pellets were completely dried in the fluid bed dryer and a small quantity of talc was added to reduce static charge. The resulting pellets were assayed for fluoxetine content and filled into capsules to provide 90 mg of fluoxetine base.

Example 2

90 mg Fluoxetine base/capsule

Bill of Materials

| | |
|---|---:|
| Cores | |
| Sucrose-starch nonpareils, 30–35 mesh | 134.19 mg |
| Fluoxetine layer | |
| Fluoxetine hydrochloride | 100.62 mg |
| Sucrose | 25.77 mg |
| Hydroxypropylmethylcellulose | 12.89 mg |
| Separating layer | |
| Hydroxypropylmethylcellulose | 6.12 mg |
| Sucrose | 18.27 mg |
| Talc, 500 mesh | 32.49 mg |
| Enteric layer | |
| HPMCAS-LF | 74.89 mg |
| Triethyl citrate | 14.96 mg |
| Talc, 500 mesh | 21.77 mg |
| Finishing layer | |
| Color mixture white (HPMC + titanium dioxide) | 43.02 mg |
| HPMC | 10.78 mg |
| Talc | Trace |
| | 493.65 mg |

The product was made substantially according to the process used in Example 1.

Example 3

| 90 mg Fluoxetine base/capsule | |
| --- | --- |
| Bill of Materials | |
| Cores | |
| Sucrose-starch nonpareils, 30–35 mesh | 121.01 mg |
| Fluoxetine layer | |
| Fluoxetine hydrochloride | 100.60 mg |
| Sucrose | 25.75 mg |
| Hydroxypropylmethylcellulose | 12.85 mg |
| Separating layer | |
| Hydroxypropylmethylcellulose | 9.48 mg |
| Sucrose | 28.38 mg |
| Talc, 500 mesh | 50.45 mg |
| Enteric layer | |
| HPMCAS-LF | 66.78 mg |
| Triethyl citrate | 13.36 mg |
| Talc, 500 mesh | 20.01 mg |
| Finishing layer | |
| Color mixture white (HPMC + titanium dioxide) | 44.30 mg |
| HPMC | 11.09 mg |
| Talc | Trace |
| | 504.06 mg |

The product was made substantially according to the process used in Example 1 with the exception that the process was scaled up and initiated with 25 kg of sucrose starch non-pareils.

Pellets made according to the above examples, and gelatin capsules filled with various batches of such pellets, have been thoroughly tested in the manners usual in pharmaceutical science. Results of stability tests show that the pellets and capsules have sufficient storage stability to be distributed, marketed and used in the conventional pharmaceutical manner.

Testing further shows that the pellets and capsules pass the conventional tests for enteric protection under conditions prevailing in the stomach. It has also been shown that the pellets release their load of fluoxetine acceptably quickly when exposed to conditions prevailing in the small intestine.

While in the foregoing specification this invention has been described in relation to certain preferred embodiments thereof, and many details have been set forth for purpose of illustration, it will be apparent to those skilled in the art that the invention is susceptible to additional embodiments and that certain of the details described herein can be varied considerably without departing from the basic principles of the invention.

What is claimed is:

1. A packaging system for storing and dispensing individual doses of medication on prescribed days, the packaging system comprising:
   a first sheet with individual doses of medication removably held thereon;
   a second sheet adapted to be folded over the first sheet;
   a plurality of labels held on either the first or second sheet, each label corresponding to one dose of medication, each of the labels being adapted to be removed from the first or second sheet and applied to a calendar to thereby serve as a reminder of the day on which the corresponding individual dose of medication is to be taken; and
   a sleeve with one open end for receiving the first and second sheets when in the folded state.

2. The system of claim 1 further comprising a spine between the first and second sheets.

3. The system of claim 2 wherein the spine bears identification information relating to the doses of medication.

4. The system of claim 1 further comprising a third sheet adapted to fold over the second or first sheet.

5. The system of claim 4 wherein the third sheet is disposed between the first and second sheets.

6. The system of claim 4 further comprising a fourth sheet with individual doses of medication removably held thereon, the fourth sheet adapted to be folded over the third sheet.

7. The system of claim 6 further comprising a spine between the second and third sheets.

8. The system of claim 4 wherein the second or third sheet bears instructional information relating to the doses of medication.

9. The system of claim 4 wherein the sleeve includes at least one notch adjacent the open end for facilitating removal of the first, second and third sheets from the sleeve.

10. The system of claim 1 wherein the sleeve has a width sufficient for the sleeve to stand independently on a flat surface.

11. The system of claim 1 wherein the height of the sleeve is generally less than ten times the width of the sleeve.

12. The system of claim 1 wherein the individual doses of medication are arranged in a pattern and the plurality of labels are arranged in a corresponding pattern.

13. The system of claim 1 wherein at least one individual dose of medication comprises the drug Fluoxetine.

14. The system of claim 1 wherein the individual dose of medication is an enteric fluoxetine pellet comprising: a) a core consisting of fluoxetine and one or more pharmaceutically acceptable excipients; b) an optional separating layer; c) an enteric layer comprising hydroxypropylmethylcellulose acetate succinate (HPMCAS) and one or more pharmaceutically acceptable excipients; d) an optional finishing layer.

15. The system of claim 14 wherein the enteric fluoxetine pellet comprises:

a core comprising

| Sucrose-starch nonpareils, 30–35 mesh | 100–150 mg |
| --- | --- |
| a Fluoxetine layer comprising | |
| Fluoxetine hydrochloride | 100.5–100.8 mg |
| Sucrose | 20–30 mg |
| Hydroxypropylmethylcellulose | 10–15 mg |
| a separating layer comprising | |
| Hydroxypropylmethylcellulose | 4–12 mg |
| Sucrose | 15–35 mg |
| Talc, 500 mesh | 25–60 mg |
| a enteric layer comprising | |
| HPMCAS-LF | 60–90 mg |
| Triethyl citrate | 10–20 mg |
| Talc, 500 mesh | 15–25 mg; and |
| a finishing layer comprising | |
| Color mixture white (HPMC + titanium dioxide) | 35–55 mg |
| HPMC | 5–15 mg |
| Talc | Trace |

16. A packaging system for storing and dispensing individual doses of medication on prescribed days, the packaging system comprising:
   a first sheet with individual doses of medication removably held thereon, each individual dose of medication having a unique mark associated therewith;
   a second sheet adapted to be folded over the first sheet; and a plurality of labels held on either the first or second sheet, each label bearing a unique mark, which unique mark corresponds with one unique mark associated with the doses of medication, each of the labels being adapted to be removed from the first or second sheet and applied to a calendar to thereby serve as a reminder of the day on which the corresponding individual dose of medication is to be taken.

17. The system of claim 16 wherein the unique marks associated with the doses of medication and the unique marks on the labels are both either matching numbers or matching letters.

18. The system of claim 16 wherein the individual doses of medication are arranged in a pattern and the plurality of labels are arranged in a corresponding pattern, wherein the unique mark on the labels is situated in generally the same location in the pattern as the one unique mark associated with the doses of medication.

19. The system of claim 16 further comprising a third sheet adapted to fold over the second or the first sheet, the third sheet bearing instructional information relating to the doses of medication.

20. The system of claim 17 further comprising a fourth sheet with individual doses of medication removably held thereon, the fourth sheet adapted to be folded over the third sheet.

21. The system of claim 16 wherein at least one individual dose of medication comprises the drug Fluoxetine.

22. The system of claim 21 wherein the individual dose of 25 medication is an enteric fluoxetine pellet comprising: a) a core consisting of fluoxetine and one or more pharmaceutically acceptable excipients; b) an optional separating layer; c) an enteric layer comprising hydroxypropylmethylcellulose acetate succinate (HPMCAS) and one or more pharmaceutically acceptable excipients; d) an optional finishing layer.

23. The system of claim 22 wherein the enteric fluoxetine pellet comprises:

| | |
|---|---|
| a core comprising | |
| Sucrose-starch nonpareils, 30–35 mesh | 100–150 mg |
| a Fluoxetine layer comprising | |
| Fluoxetine hydrochloride | 100.5–100.8 mg |
| Sucrose | 20–30 mg |
| Hydroxypropylmethylcellulose | 10–15 mg |
| a separating layer comprising | |
| Hydroxypropylmethylcellulose | 4–12 mg |
| Sucrose | 15–35 mg |
| Talc, 500 mesh | 25–60 mg |
| a enteric layer comprising | |
| HPMCAS-LF | 60–90 mg |
| Triethyl citrate | 10–20 mg |
| Talc, 500 mesh | 15–25 mg; and |
| a finishing layer comprising | |
| Color mixture white (HPMC + titanium dioxide) | 35–55 mg |
| HPMC | 5–15 mg |
| Talc | Trace |

24. The system of claim 16 further comprising a spine between the first and second sheet, the spine bearing identification information relating to the doses of medication.

25. The system of claim 24 further comprising a sleeve with one open end, the open end and the sleeve being of appropriate size and shape to matingly engage with the first and second sheet when in the folded state.

26. The system of claim 25 wherein the sleeve includes at least one notch adjacent the open end for facilitating removal of the first and second sheets from the sleeve.

27. The system of claim 25 wherein the identification information on the spine is visible when the sleeve is matingly engaged with the first and second sheets.

28. The system of claim 25 wherein the height of the sleeve is generally less than ten times the width of the sleeve.

29. A packaging system for storing and dispensing individual doses of medication on prescribed days, the packaging system comprising:

a first sheet forming a plurality of cutouts, each cutout defining an opening having an area large enough for one dose of medication to go through;

a translucent sheet overlapping a portion of the first sheet, the translucent sheet forming a plurality of blisters, the plurality of blisters arranged in a pattern on the translucent sheet, each blister having a hollow cavity upon which one dose of medication is stored and a rupturable backing sealing the hollow cavity so as to prevent contamination of the dose of medication, each rupturable backing positioned to overlap each opening;

a second sheet adapted to be folded over the first sheet;

a plurality of labels held on either the first or second sheet, each label corresponding to one dose of medication, each of the labels being adapted to be removed from the first or second sheet and applied to a calendar to thereby serve as a reminder of the day on which the corresponding individual dose of medication is to be taken; and a sleeve with one open end, the open end and the sleeve being of appropriate size and shape to receive the first and second sheet when in the folded state.

30. The system of claim 29 further comprising a spine between the first and second sheet, the spine bearing identification information relating to the doses of medication.

31. The system of claim 29 wherein the height of the sleeve is generally less than ten times the width of the sleeve.

32. The system of claim 29 further comprising a cover sheet forming a plurality of cutouts which generally conform to the shape of the plurality of blisters, the cover sheet overlapping the translucent sheet.

33. The system of claim 29 wherein each individual dose of medication has a unique mark associated therewith, each label bears a unique mark, which unique mark corresponds with one unique mark associated with the doses of medication.

34. The system of claim 29 further comprising a first individual dose of medication having a first substance, a second individual dose of medication having a second substance, wherein the first substance differs from the second substance.

35. A method for storing and dispensing individual doses of medication on prescribed days, the individual doses of medication removably held on a first sheet, the method comprising the steps of:

providing a packaging system comprising a first sheet with individual doses of medication removably held there on, each individual dose of medication having a unique mark associated therewith;

adapting a second sheet to be folded over the first sheet;

providing a plurality of labels on either the first or second sheet, each label corresponds with one dose of medication; and removing each of the labels and applying each of the labels to a calendar to thereby serve as a reminder of the day on which the corresponding individual dose of medication is to be taken.

* * * * *